(12) United States Patent
Sembo

(10) Patent No.: US 6,218,422 B1
(45) Date of Patent: Apr. 17, 2001

(54) COCKROACH CONTROLLING COMPOSITIONS

(75) Inventor: Satoshi Sembo, Takarazuka (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/553,470

(22) Filed: Apr. 20, 2000

(30) Foreign Application Priority Data

Apr. 22, 1999 (JP) .................................................. 11-114982

(51) Int. Cl.$^7$ ............................. A01N 43/38; A01N 43/08
(52) U.S. Cl. ............................................. 514/421; 514/471
(58) Field of Search ..................................... 514/421, 471

(56) References Cited

U.S. PATENT DOCUMENTS 5,532,365 * 7/1996 Kodaka et al. ...................... 544/212

FOREIGN PATENT DOCUMENTS

| 1649845 | 4/1995 | (EP) . |
| 2055822 | 3/1981 | (GB) . |

* cited by examiner

*Primary Examiner*—Allen J. Robinson
(74) *Attorney, Agent, or Firm*—Birch, Stewart, Kolasch & Birch, LLP

(57) ABSTRACT

Provided are compositions comprising 1-methyl-2-nitro-3-[(3-tetrahydrofuryl)methyl]guanidine and 3,4,5,6-tetrahydrophthalimidomethyl chrysanthemate, as well as a method of controlling cockroaches.

8 Claims, No Drawings

COCKROACH CONTROLLING COMPOSITIONS

FIELD OF THE INVENTION

The instant invention relates to compositions which may be utilized to control cockroaches.

BACKGROUND OF THE INVENTION

Various compounds and compositions have been utilized to control cockroaches, but such compounds and compositions have failed to provide effective control of cockroaches.

U.S. Pat. No. 5,532,365 discloses 1-methyl-2-nitro-3-[(3-tetrahydrofuryl)methyl]guanidine as a compound which controls insects. The pesticide Manual, $10^{th}$ ed. (pg. 968–971, published by British Crop Protection Council) discloses 3,4,5,6-tetrahydrophthalimidomethyl chrysanthemate as a an active ingredient of insecticides.

SUMMARY OF THE INVENTION

The instant invention provides compositions comprising 1-methyl-2-nitro-3-[(3-tetrahydrofuryl)methyl]guanidine and 3,4,5,6-tetrahydrophthalimidomethyl chrysanthemate. Additionally, the instant invention provides methods of controlling cockroaches comprising applying to a cockroach or to a locus of where cockroaches inhabit, 1-methyl-2-nitro-3-[(3-tetrahydrofuryl)methyl]guanidine and 3,4,5,6-tetrahydrophthalimidomethyl chrysanthemate.

DETAILED DESCRIPTION OF THE INVENTION

1-Methyl-2-nitro-3-[(3-tetrahydrofuryl)methyl]guanidine and 3,4,5,6-tetrahydrophthalimidomethyl chrysanthemate which are present in the compositions typically act as active ingredients therein. The compositions typically comprise such active ingredients so that the total amount of 1-methyl-2-nitro-3-[(3-tetrahydrofuryl)methyl]guanidine and 3,4,5,6-tetrahydrophthalimidomethyl chrysanthemate is from 0.005 to 50% by weight, wherein said percentage by weight is based on the total weight of the provided composition. In this regard, when the compositions are utilized to control cockroaches, the total amount of the active ingredients therein is typically an amount which is effective to control cockroaches. Further, the compositions typically comprise the active ingredients so that the weight-to-weight ratio of 1-methyl-2-nitro-3-[(3-tetrahydrofuryl)methyl]guanidine to 3,4,5,6-tetrahydrophthalimidomethyl chrysanthemate is from 99:1 to 1:99, preferably 9:1 to 1:9, more preferably 3:1 to 1:3. Such weight-to-weight ratios in the compositions can vary, but when said compositions are utilized to control a cockroach, said compositions generally have a sufficient weight-to-weight ratio of 1-methyl-2-nitro-3-[(3-tetrahydrofuryl)methyl]guanidine to 3,4,5,6-tetrahydrophthalimidomethyl chrysanthemate therein to provide a synergistic control over cockroaches.

Since the compositions can contain various active isomers of 3,4,5,6-tetrahydrophthalimidomethyl chrysanthemate, active stereoisomers of 3,4,5,6-tetrahydrophthalimidomethyl chrysanthemate or mixtures thereof can be utilized in the instant invention, if so desired. Examples of such stereoisomers of 3,4,5,6-tetrahydrophthalimidomethyl chrysanthemate which can be utilized in the instant invention include 3,4,5,6-tetrahydrophthalimidomethyl (1RS)-cis,trans-chrysanthemate (common name: tetramethrin), 3,4,5,6-tetrhydrophthalimidomethyl( 1R)-cis,trans-chrysanthemate, 3,4,5,6-tetrahydrophthalimidomethyl (1R)-trans-chrysanthemate and the like.

The compositions of the instant invention are typically formulated as suitable formulations of 1-methyl-2-nitro-3-[(3-tetrahydrofuryl)methyl]guanidine and 3,4,5,6-tetrahydrophthalimidomethyl chrysanthemate. Examples of such formulations of the compositions include liquid formulations, dusts, wettable powders, granules, paste formulations, microencapsulated formulations, foaming formulations, aerosols, liquid carbon dioxide solution formulations, tablets, poison baits, smoking formulations, fogging formulations, sheet formulations, resin formulations and the like. Examples of the liquid formulations of the compositions include emulsifiable concentrates, oil formulations, suspensible concentrates and the like.

Such formulations of the compositions can be produced by commonly known formulating procedures. For example, a formulation of the instant invention can be produced by mixing together 1-methyl-2-nitro-3-[(3-tetrahydrofuryl)methyl]guanidine and 3,4,5,6-tetrahydrophthalimidomethyl chrysanthemate and optionally adding thereto or mixing therewith formulation auxiliaries, carriers or the like. Based on the formulation type of the compositions, said formulations may also be produced by providing such a mixture in a suitable form, if so desired. As such, the formulations of the compositions may contain 1-methyl-2-nitro-3-[(3-tetrahydrofuryl)methyl]guanidine and 3,4,5,6-tetrahydrophthalimidomethyl chrysanthemate without additional components, but can also contain a carrier, a formulation auxiliary or the like.

Examples of formulation auxiliaries which can be utilized in the instant invention include emulsifiers, dispersing agents such as a lignin sulfonate salt and methylcellulose, adhesive agents such as carboxymethylcellulose, gum arabic, polyvinyl alcohol and polyvinyl acetate, coloring agents such as iron oxide, titanium oxide, Persian blue, alizarine dye, azo dye and phthalocyanine dye and the like. Examples of the emulsifiers which can be utilized in the instant invention include ionic emulsifiers such as an alkylsulfonate salt, alkylsulfate salt and arylsulfonate salt, nonionic emulsifiers such as a polyoxyethylene fatty acid ester, polyoxyethylenealkylaryl ether, polyoxyethylene fatty acid alcohol ether and the like.

The compositions of the instant invention generally utilize therein a carrier selected form a solid carrier, a liquid carrier and a propellant, when present.

Examples of solid carriers which can be utilized in the compositions include gelatin, vaseline, methylcellulose, lanolin, lard, natural-occurring or synthetic minerals such as clay, kaolin, talc, bentonite, sericite, quartz, sulfur, activated carbon, calcium carbonate, diatomaceous earth, pumice stone, calcite, meerschaum, dolomite, silica, alumina, vermiculite and perlite, fine granules such as granulated sawdust, corncob, coconut shell and tobacco stems and the like.

Examples of liquid carriers which can be utilized in the compositions include liquid paraffins, aromatic or aliphatic hydrocarbons such as xylene, toluene, alkylnaphthalene, phenylxylylethane, kerosene, gas oils, hexane and cyclohexane, halogenated hydrocarbons such as chlorobenzene, dichloromethane, dichloroethane and trichloroethane, alcohols such as methanol, ethanol, isopropyl alcohol, butanol, hexanol and ethylene glycol, ethers such as diethyl ether, ethylene glycol dimethyl ether, diethylene glycol monomethyl ether, diethylene glycol monoethyl ether, propylene glycol monomethyl ether, tetrahydrofuran and dioxane, esters such as ethyl acetate and butyl acetate, ketones such as acetone, methyl ethyl ketone, methyl isobutyl ketone and cyclohexanone, nitriles such as acetonitrile and isobutyronitrile, amides such as N,N-dimethylformamide and N,N-dimethylacetamide, botanical oils such as soybean oil and cotton seed oil, botanical essential oils such as orange oil, hyssop oil and lemon oil, water, sulfoxides such as dimethyl sulfoxide and the like.

Examples of propellants which can be utilized in the compositions include propane gas, butane gas, flon gas, liquefied petroleum gas (LPG), dimethyl ether, carbonate gas and the like. By utilizing the propellant in the compositions, the compositions may be formulated into foaming formulations, aerosols and the like.

When formulating the compositions as poison baits, said poison bait can additionally contain a bait ingredient, anti-oxidant, preservative, agent for averting unintentional child or pet ingestion of the poison bait, cockroach attractant fragrance or the like. Examples of bait ingredients which can be utilized in said poison baits include powdered crop, botanical oil, sugar, crystallized cellulose and the like. Examples of anti-oxidants which can be utilized in said poison baits include dibutylhydroxytoluene, nordihydroguaiaretic acid and the like. As an example of a preservative which can be utilized in said poison baits, there is included dehydroacetic acid and the like. As an example of an agent for averting unintentional child or pet ingestion of the poison bait which can be utilized in said poison baits, there is included powdered pepper and the like. Examples of cockroach attractant fragrances which can be utilized in said poison baits include cheese fragrances, onion fragrances and the like.

When formulating the compositions as resin formulations, said resin formulation can additionally contain a resin material such as a polyvinyl chloride or polyurethane. Furthermore, the polyvinyl chloride and polyurethane when utilized in the compositions may optionally have a plasticizer added thereto. Examples of plasticizers which can be utilized in the instant invention include phthalate esters such as dimethyl phthate and dioctyl phthate, adipate esters, stearate esters and the like.

Such resin formulations of the compositions can be formulated by mixing together 1-methyl-2-nitro-3-[(3-tetrahydrofuryl)methyl]guanidine, 3,4,5,6-tetrahydrophthalimidomethyl chrysanthemate and said resin material, and forming the resulting mixture into a desired form. For example, the resin formulations may be formulated by mixing together 1-methyl-2-nitro-3-[(3-tetrahydrofuryl)methyl]guanidine, 3,4,5,6-tetrahydrophthalimidomethyl chrysanthemate and said resin material by using a standard kneading machine and then be formed into a desired form by employing a molding process. Examples of known molding processes which can be employed to formulate the resin formulations include ejection molding, extrusion molding, press molding and the like. The resin formulations of the instant invention can be further formed by additional molding or cutting. Examples of such resin formulations of the instant invention include board formulations, film formulations, tape formulations, rope formulations, net formulations, sheet formulations and the like.

When utilizing 1-methyl-2-nitro-3-[(3tetrahydrofuryl)methyl]guanidine and 3,4,5,6-tetrahydrophthalimidomethyl chrysanthemate together to control cockroaches, 1-methyl-2-nitro-3-[(3-tetrahydrofuryl)methyl]guanidine and 3,4,5,6-tetrahydrophthalimidomethyl chrysanthemate are applied to at least one cockroach or a locus where a control of a cockroach is desired. As such, 1-methyl-2-nitro-3-[(3-tetrahydrofuryl)methyl]guanidine and 3,4,5,6-tetrahydrophthalimidomethyl chrysanthemate may be utilized to control cockroaches by applying the composition to the cockroach or to a habitat of said cockroach. Furthermore, 1-methyl-2-nitro-3-[(3-tetrahydrofuryl)methyl]guanidine and 3,4,5,6-tetrahydrophthalimidomethyl chrysanthemate may also be utilized to control cockroaches by adding 1-methyl-2-nitro-3-[(3-tetrahydrofuryl)methyl]guanidine and 3,4,5,6-tetrahydrophthalimidomethyl chrysanthemate to products in which a control of cockroaches is desired. In such cases, 1-methyl-2-nitro-3-[(3-tetrahydrofuryl)methyl]guanidine and 3,4,5,6-tetrahydrophthalimidomethyl chrysanthemate may be added to synthetic resin sheets to give various cockroach-proof products.

In utilizing 1-methyl-2-nitro-3-[(3-tetrahydrofuryl)methyl]guanidine and 3,4,5,6-tetrahydrophthalimidomethyl chrysanthemate to control cockroaches in the household area, 1-methyl-2-nitro-3-[(3-tetrahydrofuryl)methyl]guanidine and 3,4,5,6-tetrahydrophthalimidomethyl chrysanthemate are utilized in a total amount which can effectively control cockroaches. Such an amount of 1-methyl-2-nitro-3-[(3-tetrahydrofuryl)methyl]guanidine and 3,4,5,6-tetrahydrophthalimidomethyl chrysanthemate which can effectively control cockroaches is typically an amount of from 0.001 to 100 mg/m$^3$. Said emulsifiable concentrates, wettable powders, flowables, microencapsulated formulations and the like are usually diluted so that 1-methyl-2-nitro-3-[(3-tetrahydrofuryl)methyl]guanidine and 3,4,5,6-tetrahydrophthalimidomethyl chrysanthemate can be applied at a concentration of from 0.1 to 1000 ppm. In diluting such formulations of the instant invention, said formulations may be diluted with water, if so desired. Further, said oil formulations, aerosols, fogging formulations, poison baits, sheet formulations and the like usually utilize 1-methyl-2-nitro-3-[(3-tetrahydrofuryl)methyl]guanidine and 3,4,5,6-tetrahydrophthalimidomethyl chrysanthemate together to control cockroaches without dilution.

In utilizing the compositions to control cockroaches, examples of such cockroaches include German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*) and the like.

It should be noted that 1-methyl-2-nitro-3-[(3-tetrahydrofuryl)methyl]guanidine and 3,4,5,6-tetrahydrophthalimidomethyl chrysanthemate can be applied together to a cockroach or a locus where cockroaches inhabit by employing various methods. For example, as a method of applying 1-methyl-2-nitro-3-[(3-tetrahydrofuryl)methyl]guanidine and 3,4,5,6-tetrahydrophthalimidomethyl chrysanthemate, there are mentioned methods which have said active ingredients applied to a locus as a mixture of the instant invention or as separately in a sequential manner. As an example of the latter type of method, at least one of the active ingredients is applied to a locus and then the other active ingredient(s) is applied to said locus. Such latter type of the methods include applying 1-methyl-2-nitro-3-[(3tetrahydrofuryl)methyl]guanidine and the compound of formula (I) to a locus in a separate but essentially simultaneous manner, wherein the active ingredients are present in separate compositions which arc applied to a locus at an essentially simultaneous time or within an essentially simultaneous timeframe.

Furthermore, the compositions may also comprise at least one additional cockroach controlling ingredient or synergist. Examples of such additional cockroach controlling ingredients which may be utilized in the compositions include organophosphorous compounds, carbamate compounds, N-phenylpyrazole compounds and the like. Examples of organophosphorous compounds which may be utilized in the compositions include dichlorvos, tetrachlorovinphos, fenthion, chlorpyrifos, diazinon and the like. Examples of carbamate compounds which may be utilized in the compositions include propoxur, carbaryl, metoxadiazone, fenobucarb and the like. Examples of synergists which may be utilized in the compositions include PBO, S421, MGK 264, IBTA and the like.

EXAMPLES

Formulation Example 1

Emulsifiable Concentrate

Two and one-half (2.5) parts by weight of 1-methyl-2-nitro-3-[(3-tetrahydrofuryl)methyl]guanidine, 2.5 parts by weight of 3,4,5,6-tetrahydrophthalimidomethyl (1R)-cis,trans-chrysanthemate, 8 parts by weight of polyoxyethylenealkylaryl ether, 2 parts by weight of sodium alkylarylsulfonate and 85 parts by weight of xylene are mixed together to provide an emulsifiable concentrate of the instant invention.

Formulation Example 2

Aerosol

One-tenth (0.1) part by weight of 1-methyl-2-nitro-3-[(3-tetrahydrofuryl)methyl]guanidine, 0.1 part by weight of 3,4,5,6-tetrahydrophthalimidomethyl chrysanthemate, 30 parts by weight of isopropyl alcohol and 29.8 parts by weight of distilled water are mixed together, are dissolved therein and are placed in an aerosol container. A valve component is connected to the aerosol container and 40 parts by weight of liquefied petroleum gas (LPG) is packed into the aerosol container, to provide a water-based aerosol formulation of the instant invention.

Formulation Example 3

Fogging Formulation

Five (5) parts by weight of 1-methyl-2-nitro-3-[(3-tetrahydrofuryl)methyl]guanidine, 5 parts by weight of 3,4,5,6-tetrahydrophthalimidomethyl chrysanthemate, 7 parts by weight of ethyl oleate, 0.5 parts by weight of zinc oxide and 2 parts by weight of α-starch are mixed together in a foaming agent to an amount of 100 parts by weight. Water is added to the mixture. Subsequently, the mixture is kneaded, is formed into granules with an extrusion machine and is allowed to dry. In a container sectioned by an aluminum wall divider, 2 grams of said granules are placed into one section thereof and 50 grams of magnesium oxide are placed into the other section thereof, to provide a fogging formulation.

Test Example 1

Diethylene glycol monoethyl ether solutions either containing 0.4% weight by volume (w/v) of 1-methyl-2-nitro-3-[(3-tetrahydrofuryl)methyl]guanidine or 0.4% weight by volume (w/v) of 3,4,5,6-tetrahydrophthalimidomethyl (1R)-cis,trans-chrysanthemate were produced. Solutions were prepared by mixing together, respectively, the solutions containing 1-methyl-2-nitro-3-[(3-tetrahydrofuryl)methyl]guanidine and the solutions containing 3,4,5,6-tetrahydrophthalimidomethyl (1R)-cis,trans-chrysanthemate at ratios of 1:3, 1:1 and 3:1, as provided in Table 1. The solutions and the prepared solution mixtures were diluted with appropriate amounts of distilled water. In the diluted solutions, the concentrations in percent weight by volume (%w/v) of 1-methyl-2-nitro-3-[(3-tetrahydrofuryl)methyl]guanidine therein corresponding to 3,4,5,6-tetrahydrophthalimidomethyl (1R)-cis,trans-chrysanthemate therein were 0.1/0, 0.2/0, 0.15/0.05, 0.1/0.1, 0.05/0.15, 0/0.1 and 0/0.2, as provided in Table 1.

Triangular column shaped wooden containers containing 5 male and 5 female German cockroaches (*Blattela germanica*) therein were placed, respectively, upright in the central region of cubic glass boxes which posses a volume of 0.34 m$^3$ and a side length of 70 cm, and in which said triangular column shaped wooden container possesses a substantially equilateral triangle base, a side length of 3.5 cm and a height of 15 cm. Four and one-fifth milliliters (4.2 mL) of the prepared solutions were sprayed, respectively, into the glass boxes with a spray gun. Ten (10) minutes after spraying the compositions, the cockroaches were transferred, respectively, to sanitary containers and were provided with water and food. The mortality rates of the cockroaches were observed 1 day thereafter. The results are shown in Table 1.

TABLE 1

| Compound A*/Compound B** | | Cockroach mortality |
| --- | --- | --- |
| mixing ratio | concentration (% w/v) | rate (%) |
| 100:0 | 0.1/0 | 30 |
| 100:0 | 0.2/0 | 40 |
| 75:25 | 0.15/0.05 | 90 |
| 50:50 | 0.1/0.1 | 100 |
| 25:75 | 0.05/0.15 | 100 |
| 0:100 | 0/0.1 | 0 |
| 0:100 | 0/0.2 | 40 |

*Compound A represents 1-methyl-2-nitro-3-[(3-tetrahydrofuryl)methyl]guanidine
**Compound B represents 3,4,5,6-tetrahydrophthalimidomethyl (1R)-cis, transchrysanthemate

Comparative Example

Diethylene glycol monoethyl ether solutions either containing 0.1% weight by volume (w/v) of 1-methyl-2-nitro-3-[(3-tetrahydrofuryl)methyl]guanidine or 0.1% weight by volume (w/v) of 3,4,5,6-tetrahydrophthalimidomethyl (1R)-cis,trans-chrysanthemate were produced. A solution was was then prepared by mixing together, respectively, one of the solutions containing 1-methyl-2-nitro-3-[(3-tetrahydrofuryl)methyl]guanidine and one of the solutions containing 3,4,5,6-tetrahydrophthalimidomethyl (1R)-cis,trans-chrysanthemate at a ratio of 1:1, as provided in Table 1. The solutions and the prepared solution mixture were diluted with appropriate amounts of distilled water. In the resulting solutions, the concentrations in percent weight by volume (%w/v) of 1-methyl-2-nitro-3-[(3 -tetrahydrofuryl)methyl]guanidine therein corresponding to 3,4,5,6-tetrahydrophthalimidomethyl (1R)-cis,trans-chrysanthemate therein were 0.05/0, 0.1/0, 0.05/0.05, 0/0.05 and 0/0.1, as provided in Table 2.

In cubic glass boxes possessing a volume of 0.34 m$^3$ and a side length of 70 cm, 10 male and 10 female adult houseflies (*Musca domestica*) were released therein, respectively. Two and one-tenth milliliters (2.1 mL) of the prepared diluted solutions are sprayed, respectively, into the glass boxes with a spray gun. Ten minutes after spraying the prepared solutions, the houseflies were transferred, respectively, to sanitary containers and were provided with water and food. The mortality rate of the houseflies were observed 1 day thereafter. The results are shown in Table 2.

TABLE 2

| Compound A*/Compound B** | | Housefly Mortality |
|---|---|---|
| mixing ratio | concentration (% w/v) | Rate (%) |
| 100:0 | 0.05/0 | 88.1 |
| 100:0 | 0.1/0 | 96.6 |
| 50:50 | 0.05/0.05 | 95 |
| 0:100 | 0/0.05 | 93.3 |
| 0:100 | 0/0.1 | 100 |

*Compound A represents 1-methyl-2-nitro-3-[(3-tetrahydrofuryl)methyl]guanidine
**Compound B represents 3,4,5,6-tetrahydrophthalimidomethyl (1R)-cis,transchrysanthemate The above test results from the Comparative Example evidence that a composition containing 1-methyl-2-nitro-3-[(3-tetrahydrofuryl)methyl]guanidine and 3,4,5,6-tetrahydrophthalimidomethyl (1R)-cis,trans-chrysanthemate therein does not provide a synergistic control over houseflies.

What is claimed is:

1. A cockroach-controlling composition comprising synergistically effective cockroach controlling amounts of 1-methyl-2-nitro-3-((3-tetrahydrofuryl)methyl)guanidine and 3,4,5,6-tetrahydrophthalimidomethyl chrysanthemate.

2. A composition according to claim 1, wherein a weight-to-weight ratio of 1-methyl-2-nitro-3-[(3-tetrahydrofuryl)methyl]guanidine to 3,4,5,6-tetrahydrophthalimidomethyl chrysanthemate is 99:1 to 1:99.

3. A composition according to claim 1, wherein a weight-to-weight ratio of 1-methyl-2-nitro-3-[(3-tetrahydrofuryl)methyl]guanidine to 3,4,5,6-tetrahydrophthalimidomethyl chrysanthemate is 9:1 to 1:9.

4. A composition according to claim 1, wherein a weight-to-weight ratio of 1-methyl-2-nitro-3-[(3-tetrahydrofuryl)methyl]guanidine to 3,4,5,6-tetrahydrophthalimidomethyl chrysanthemate is 3:1 to 1:3.

5. A method of controlling a cockroach, the method comprising:

applying to a cockroach or a locus where cockroaches inhabit, synergistically effective cockroach controlling amounts of 1-methyl-2-nitro-3-((3-tetrahydrofuryl)methyl)guanidine and 3,4,5,6-tetrahydrophthalimidomethyl chrysanthemate.

6. A method according to claim 5, wherein a weight-to-weight ratio of 1-methyl-2-nitro-3-[(3-tetrahydrofuryl)methyl]guanidine to 3,4,5,6-tetrahydrophthalimidomethyl chrysanthemate is 99:1 to 1:99.

7. A method according to claim 5, wherein a weight-to-weight ratio of 1-methyl-2-nitro-3-[(3-tetrahydrofuryl)methyl]guanidine to 3,4,5,6-tetrahydrophthalimidomethyl chrysanthemate is 9:1 to 1:9.

8. A method according to claim 5, wherein a weight-to-weight ratio of 1-methyl-2-nitro-3-[(3-tetrahydrofuryl)methyl]guanidine to 3,4,5,6-tetrahydrophthalimidomethyl chrysanthemate is 3:1 to 1:3.

* * * * *